US005793781A

United States Patent [19]
Lawandy

[11] Patent Number: 5,793,781
[45] Date of Patent: Aug. 11, 1998

[54] SOLID STATE SOURCE FOR GENERATING INTENSE LIGHT FOR PHOTODYNAMIC THERAPY AND PHOTOMEDICINE

[75] Inventor: Nabil M. Lawandy, North Kingston, R.I.

[73] Assignee: Spectra Science Corporation, Providence, R.I.

[21] Appl. No.: 788,208

[22] Filed: Jan. 24, 1997

[51] Int. Cl.⁶ .................................................. H01S 3/10
[52] U.S. Cl. ............................. 372/22; 372/39; 372/93; 372/3
[58] Field of Search ........................... 372/69, 39, 22, 372/93, 92, 3

[56] References Cited

U.S. PATENT DOCUMENTS 5,448,582  9/1995  Lawanmdy .................................. 372/39

OTHER PUBLICATIONS

"Solid-state barium nitrate Raman laser in the visible region", Chuan He, Thomas H. Chyba, Optics Communications 135 (1997), pp. 273–378.

"Stimulated Raman scattering of picosecond pulses in barium nitrate crystals", Petr G. Zverev et al., Optics Communications 97 (1993), 59–64.

"Stimulated Reman scattering of the beam from a copper-vapor laser in a barium nitrate crystal", S.A. Vitsinskii et al., Quantum Electron, 23 (12), Dec. 1993, 1001–1004.

"Generation of radiation in a resonator under conditions of stimulated Raman scattering in $Ba(NO_3)_2$, $NaNO_3$, and $CaCO_3$ crystals", S.N. Karpukhin et al., Sov. J. Quantum Electron., 16(8), Aug. 1986, 1027–1030.

"Conversion of tunable radiation from a laser utilizing an LiF crystal containing $F_2$ color centers by stimulated Raman scattering in $Ba(No_3)_2$ and $KGd(WO_4)_2$ crystals", T.T. Basiev et al., Sov. J. Quantum Electron., 17(12), Dec. 1987, 1560–1561.

Primary Examiner—Leon Scott, Jr.
Attorney, Agent, or Firm—Perman & Green, LLP

[57] ABSTRACT

This invention teaches an optical source (10) for performing photomedicine. The optical source includes a Nd:YLF laser (12) having an output providing light having a wavelength of 1.053 micrometers; a frequency doubler (13) that is optically coupled to the laser output for converting a portion of the light to frequency doubled light, the frequency doubler having an output providing frequency doubled light having a wavelength of 526.5 nm; and, coupled to the output of the frequency doubler, a unit (14) for shifting the frequency doubled light to light having a wavelength of about 630 nm. In a presently preferred embodiment of this invention the shifting unit includes a device for performing stimulated Raman scattering of the frequency doubled light for creating the third Stokes line at 630.1 nm. The device includes a crystal comprised of a $R_x(MO_3)_y$ compound and means for establishing a multi-pass or resonant cavity optical configuration through the crystal. By example, the crystal is comprised of one of $Ba(NO_3)_2$, $KNO_3$, $Ca(O_3)$, $Pb(NO_3)_2$, and $NaNO_3$.

20 Claims, 1 Drawing Sheet

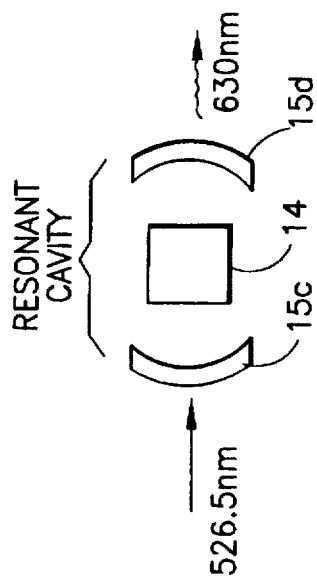
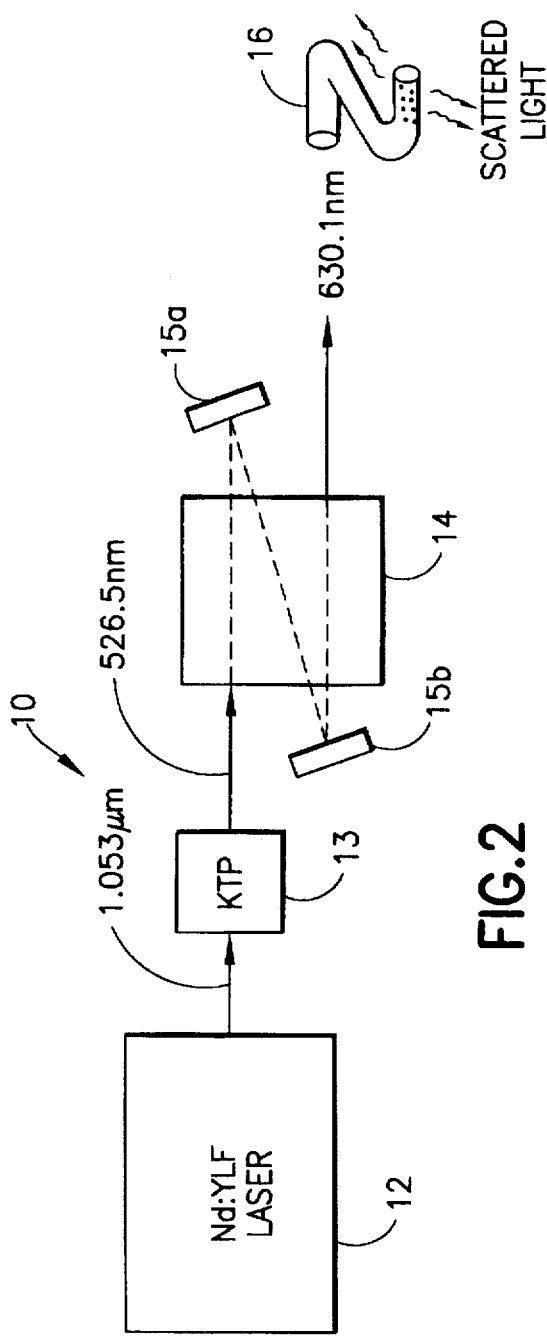
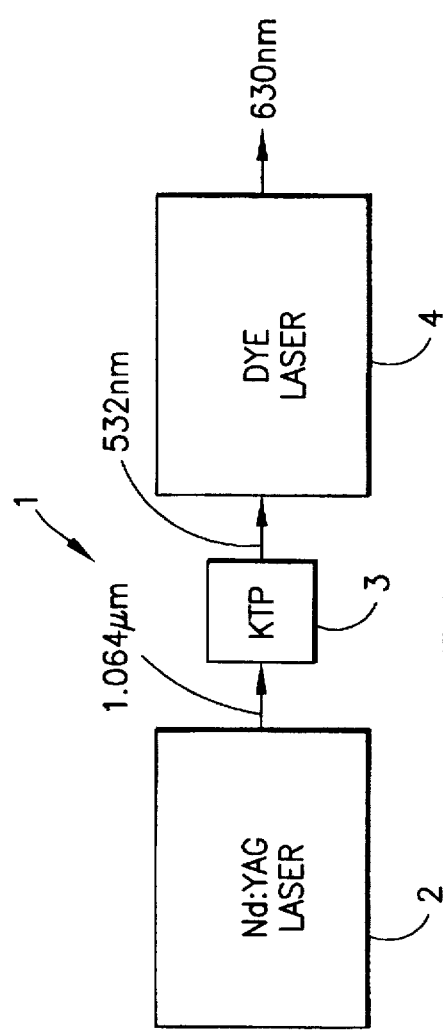

SOLID STATE SOURCE FOR GENERATING INTENSE LIGHT FOR PHOTODYNAMIC THERAPY AND PHOTOMEDICINE

FIELD OF THE INVENTION

This invention relates generally to optically-based therapeutic procedures.

BACKGROUND OF THE INVENTION:

Photodynamic Therapy (PDT) uses specifically designed drugs such as Foscan® (Scotia Pharmaceuticals), ALA (DUSA) and Photofrin (QLT Phototherapeutics) to destroy rapidly dividing cells. These drugs are selectively retained or generated at rapidly dividing cells and are subsequently excited by light to produce the desired effects. The primary mode of activity usually involves energy transfer from these photoexcited drugs to $O_2$ to produce superoxides or $O_2$ in its singlet state. To date this excitation has been provided by lasers, lamps, and new materials such as LaserPaint™ (laser action in amplifying scattering media). Some of these sources are generally expensive and require complicated delivery systems.

Two of the most important photodynamic therapy drugs are the naturally occurring ALA compound and Photofrin. Both of these are porphyrin compounds that have a peak absorption at 630 nm with a linewidth of approximately 35 nm.

Photofrin has recently received FDA approval for the treatment of esophageal cancer. As such, a low cost optical source at 630 nm has become a very important goal.

FIG. 1 illustrates a conventional optical source 1 that is suitable for use with Photofrin and similar photodynamic therapy drugs. The source 1 includes a pulsed (e.g., 150 nanosecond pulse width, 25 KHz pulse repetition rate) Nd:YAG laser 2 that outputs 1.064 μm light to a frequency doubler, such as a KTP crystal 3. The 532 nm output of the KTP crystal 3 is used to drive a dye laser 4, which provides the desired 630 nm light at the required power.

As those skilled in the art will appreciate, the use of the dye laser 4 has a number of disadvantages, including high initial and operating expense, a required use of fluids, pumps and plumbing, and a frequent need for service.

OBJECTS AND ADVANTAGES OF THE INVENTION

It is a first object and advantage of this invention to provide a nominally 630 nm optical source that overcomes the foregoing and other problems.

It is a second object and advantage of this invention to provide a lower cost, essentially solid state optical source providing optical radiation for a photomedicine and/or phototherapeutic application.

It is a further object and advantage of this invention to provide a lower cost, essentially solid state optical source providing 630 nm radiation for exciting Photofrin and similar phototherapeutic drugs.

SUMMARY OF THE INVENTION

The foregoing and other problems are overcome and the objects of the invention are realized by methods and apparatus in accordance with embodiments of this invention.

In a first aspect this invention teaches an optical source for performing photomedicine. The optical source includes, by example, a Nd:YLF laser having an output providing light having a wavelength of 1.053 micrometers; a frequency doubler that is optically coupled to the laser output for converting a portion of the light to frequency doubled light, the frequency doubler having an output providing frequency doubled light having a wavelength of 526.5 nm; and, coupled to the output of the frequency doubler, a unit for shifting the frequency doubled light to light having a wavelength of about 630 nm, in one embodiment, or, in another embodiment, to a wavelength of about 675 nm.

In a presently preferred embodiment of this invention the shifting unit includes a device for performing stimulated Raman scattering of the frequency doubled light for creating the third Stokes line at 630.1 nm, or the fourth Stokes line at 675 nm. The device includes a crystal comprised of a $R_x(MO_3)y$ compound and means for establishing a multi-pass or resonant cavity optical configuration with the crystal. By example, the crystal is comprised of one of $Ba(NO_3)_2$, $KNO_3$, $Ca(O_3)$, $Pb(NO_3)_2$, and $NaNO_3$.

In a second aspect this invention teaches a method for providing an optical source for performing photomedicine. The method includes the steps of: (a) modifying a Nd:YAG laser by replacing the laser rod with a Nd:YLF laser rod capable of providing light having a wavelength of 1.053 micrometers; (b) phase matching a frequency doubler to the Nd:YLF emission to provide frequency doubled light having a wavelength of 526.5 nm; and (c) shifting the frequency doubled light to light having a wavelength of about 630 nm for exciting a phototherapeutic compound.

BRIEF DESCRIPTION OF THE DRAWINGS

The above set forth and other features of the invention are made more apparent in the ensuing Detailed Description of the Invention when read in conjunction with the attached Drawings, wherein:

FIG. 1 is simplified block diagram of a prior art 630 nm optical source suitable for use in a phototherapeutic application;

FIG. 2 is simplified block diagram of an improved 630 nm optical source that is constructed in accordance with this invention, the improved source also being suitable for use in a phototherapeutic application; and FIG. 3 illustrates a resonant cavity embodiment of a unit for providing Raman scattering.

DETAILED DESCRIPTION OF THE INVENTION

Referring to FIG. 2, in an improved optical source 10 the Nd:YAG laser 1 is replaced with a Nd:YLF laser 12 (i.e., Yttrium Lanthanum Fluoride (YLiF$^4$) in a Nd$^{3+}$ laser host material). The entire laser may be replaced or, in accordance with an aspect of this invention, the laser 1 of FIG. 1 is retrofitted by removing the Nd:YAG laser rod and replacing same with an equivalent Nd:YLF laser rod. The Nd:YLF laser 12 operates at 1.053 μm, and may have a 100–300 nanosecond pulse width and a 10–30 KHz pulse repetition rate. A suitable output power of the Nd:YLF laser is in the range of about 5 W to about 100 W (for 25 KHz operation). The output of the Nd:YLF laser 12 is frequency doubled, such as with a KTP crystal 13 or an equivalent frequency doubler. The 526.5 nm output of the crystal 13 is then shifted by stimulated Raman scattering or an equivalent technique with a $Ba(NO_3)_2$ (or equivalent) crystal 14 to nominally 630 nm (i.e., 630.1 nm). In one embodiment the Raman shifting is accomplished in a multi-pass configuration (i.e., three passes through the $Ba(NO_3)_2$ (or equivalent) crystal 14.

Thus, mirrors 15a and 15b are provided to establish a suitable multi-pass optical path. It is also within the scope of this invention to accomplish the Raman shifting in a resonant cavity configuration, as shown more particularly in FIG. 3. The 630 nm light (having a power of at least 100 mW to several Watts) is then directed into an optical fiber, catheter, or any suitable device 16 for delivering the 630 nm light to a region to be treated. By example, the device 16 may be a catheter having a scattering region for scattering the 630 nm light at the region of tissue to be treated.

In greater detail, the Ba(NO$_3$)$_2$ crystal 14 (nominally about 1–5 cm in length) is employed to Raman shift the output of the solid state laser 12 to the required wavelengths for general photomedicine applications and, in particular, to the wavelengths required for photodynamic therapy. The technique relies on the exceptionally high Raman scattering cross-section of Ba(NO$_3$)$_2$ which provides a Stokes shift of 1047 cm$^{-1}$. This large cross-section is primarily attributed to the narrow linewidth of the transition (approximately 1.5 cm$^{-1}$) at room temperature. The large cross-section has been used to drive stimulated Raman scattering in centimeter lengths of Ba(NO$_3$)$_2$ material, both in a single pass and resonant cavity configuration.

General reference may be had in this regard to the following publications: "Stimulated Raman scattering of picosecond pulses in barium nitrate crystals", Petr G. Zverev et al., Optics Communications 97 (1993), 59–64; "Stimulated Raman scattering of the beam from a copper-vapor laser in a barium nitrate crystal", S. A. Vitsinskii et al., Quantum Electron, 23 (12), December 1993, 1001–1004; "Generation of radiation in a resonator under conditions of stimulated Raman scattering in Ba(NO$_3$)$_2$, NaNO$_3$, and CaCO$_3$ crystals", S. N. Karpukhin et al., Sov. J. Quantum Electron., 16(8), August 1986, 1027–1030; and "Conversion of tunable radiation from a laser utilizing an LiF crystal containing F$_2$ color centers by stimulated Raman scattering in Ba(NO$_3$)$_2$ and KGd(WO$_4$)$_2$ crystals", T. T. Basiev et al., Sov. J. Quantum Electron., 17(12), December 1987, 1560–1561.

In accordance with an aspect of the invention, a multi-pass configuration is used which allows for the generation of the desired wavelength or wavelengths (e.g., 630.1 nm) by several Stokes Raman conversions (in particular, three Stokes Raman conversions for the photodynamic therapy drug Photofrin).

Continuing this process to the fourth Stokes line of 526.5 nm generates 675 nanometers, a wavelength that is expected to be useful for the excitation of the benzoporphyrin derivative (BPD), a photosynthesizer used for prostrate, psoriasis, and macular degeneration conditions.

As was noted previously, a resonant cavity configuration as in FIG. 3 can also be employed. In this embodiment the crystal 14 is disposed between mirrors 15c and 15d, which define a resonant cavity around the crystal 14. Mirror 15c, a dichroic mirror, is transmissive to the input frequency doubled light, and is reflective to the Stokes lines of interest (e.g., lines 1–3 for the 630 nm embodiment and lines 1–4 for the 675 nm embodiment). Mirror 15d is partially transmissive to the Stokes line (e.g., third or fourth) that is the desired therapeutic wavelength.

A specific case is the illustrated use of the Nd:YLF laser 12 which is frequency doubled to 526.5 nm as a pump source. A three pass geometry is used to create the third Stokes line at 630.1 nm, with conversion efficiencies exceeding 25%. The 630.1 nm wavelength is an optimum wavelength for Photofrin excitation. Other configurations can be used, such as cavities or multi-pass White cells, to produce the desired wavelengths. These modifications are well within the capabilities of those skilled in the art, when guided by the teachings of this invention.

A further aspect of this invention is an ability to directly adapt or retrofit an existing installed base of Nd:YAG lasers to become pump lasers for generating the desired 630 nm light. The retrofit process involves (a) replacing the Nd:YAG rod in the laser 1 with the Nd:YLF rod, (b) adjusting the KTP crystal for phase matching to the emission from the Nd:YLF rod (by adjusting the KTP crystal angle to about 21°); and (c) placing the Ba(NO$_3$)$_2$ converter assembly 14, 15a, 15b (or 14, 15c, 15d) after the KTP crystal 13. Using this technique it is possible to obtain, at 630 nm, output powers as high as several watts at kilohertz repetition rates. Such a conversion package is significantly less costly than a dye laser (e.g., by a factor of 12:1), and can be installed in, typically, less than one hour of service time.

The teaching of this invention is also useable with higher pulse energy Nd:YLF lasers which operate at low repetition rates (~30 Hz). These sources provide equivalent average powers at 630 nm, but have the advantage of being very compact and cost effective.

Finally, the operation of such a higher energy, low repetition rate pulsed Nd:YLF laser, with combined frequency doubling and Raman shifting in Ba(NO$_3$)$_2$, or any other R$_x$(MO$_3$)$_y$ compounds (such as KNO$_3$, Ca(O$_3$), Pb(NO$_3$)$_2$, and NaNO$_3$) can produce other desirable wavelengths for photomedicine directly, or by serving as a pump source for LaserPaint™ materials (amplifying/scattering media), as described in U.S. Pat. No. 5,448,582.

Although described in the context of a Nd:YLF laser, it should be appreciated that the Nd$^{3+}$ laser host material may be doped with other compounds to yield other combinations of emission, frequency doubled, and shifted wavelengths. As such, and although the presently preferred embodiment of this invention employs the Nd:YLF laser, it is within the scope of this invention to use other lasing materials in order to obtain a desired wavelength of phototherapeutic light.

It is also within the scope of this invention to employ a diode-pumped laser, such as a diode-pumped YLF laser, as the pump source 12. A diode-pumped YLF operating in the mJ range at kilohertz repetition rates is a suitable choice.

Thus, while the invention has been particularly shown and described with respect to preferred embodiments thereof, it will be understood by those skilled in the art that changes in form and details may be made therein without departing from the scope and spirit of the invention.

What is claimed is:

1. An optical source for performing photomedicine, comprising:
    a Nd:YLF laser having an output providing light having a wavelength of 1.053 micrometers;
    a frequency doubler that is optically coupled to said laser output for converting a portion of the light to frequency doubled light, said frequency doubler having an output providing frequency doubled light having a wavelength of 526.5 nm; and
    coupled to said output of said frequency doubler, means for shifting the frequency doubled light to light having a longer wavelength selected for exciting a phototherapeutic compound.

2. An optical source as set forth in claim 1, wherein the longer wavelength is about 630 nm.

3. An optical source as set forth in claim 1, wherein the longer wavelength is about 675 nm.

4. An optical source as set forth in claim 1, wherein said shifting means is comprised of means for performing stimulated Raman scattering.

5. An optical source as set forth in claim 1, wherein said shifting means is comprised of means for creating the third Stokes line at 630.1 nm.

6. An optical source as set forth in claim 1, wherein said shifting means is comprised of means for creating the fourth Stokes line at 675 nm.

7. An optical source as set forth in claim 1, wherein said shifting means is comprised of:
a crystal comprised of a $R_x(MO_3)_y$ compound; and
means for establishing a multi-pass optical configuration through said crystal.

8. An optical source as set forth in claim 1, wherein said shifting means is comprised of:
a crystal comprised of a $R_x(MO_3)_y$ compound; and
means for establishing a resonant cavity around said crystal.

9. An optical source as set forth in claim 7, wherein said crystal is comprised of one of $Ba(NO_3)_2$, $KNO_3$, $Ca(O_3)$, $Pb(NO_3)_2$, and $NaNO_3$.

10. An optical source as set forth in claim 8, wherein said crystal is comprised of one of $Ba(NO_3)_2$, $KNO_3$, $Ca(O_3)$, $Pb(NO_3)_2$, and $NaNO_3$.

11. A method for providing an optical source for performing photomedicine, comprising the steps of:
modifying a laser by replacing a Nd:YAG laser rod with a Nd:YLF laser rod capable of providing light having a wavelength of 1.053 micrometers;
phase matching a frequency doubler to the Nd:YLF emission to provide frequency doubled light having a wavelength of 526.5 nm; and
shifting the frequency doubled light to light having a wavelength in the range of about 630 nm to about 675 nm for exciting a phototherapeutic compound of interest.

12. A method as set forth in claim 11, wherein the step of shifting includes a step of performing stimulated Raman scattering.

13. A method as set forth in claim 11, wherein the step of shifting includes a step of creating the third Stokes line at 630.1 nm.

14. A method as set forth in claim 11, wherein the step of shifting includes a step of creating the fourth Stokes line at 675 nm.

15. A method as set forth in claim 11, wherein the step of shifting includes the preliminary steps of:
providing a crystal comprised of a $R_x(MO_3)_y$ compound; and
establishing a multi-pass optical configuration through the crystal.

16. A method as set forth in claim 11, wherein the step of shifting includes the preliminary steps of:
providing a crystal comprised of a $R_x(MO_3)_y$ compound; and
establishing a resonant cavity around the crystal.

17. A method as set forth in claim 15, wherein the step of providing a crystal provides a crystal comprised of one of $Ba(NO_3)_2$, $KNO_3$, $Ca(O_3)$, $Pb(NO_3)_2$, and $NaNO_3$.

18. A method as set forth in claim 16, wherein the step of providing a crystal provides a crystal comprised of one of $Ba(NO_3)_2$, $KNO_3$, $Ca(O_3)$, $Pb(NO_3)_2$, and $NaNO_3$.

19. A method as set forth in claim 11, and further comprising steps of:
applying the light having a wavelength in the range of about 630 nm to about 675 nm to an input of an optical conductor;
conveying the light to a region of tissue treated with the phototherapeutic compound of interest; and
scattering the light at the region of tissue.

20. A solid state optical source for performing photomedicine, comprising:
a pump laser having an output providing light having a first wavelength;
a frequency doubler that is optically coupled to said pump laser output for converting a portion of the light having the first wavelength to frequency doubled light at an output of said frequency doubler; and
coupled to said output of said frequency doubler, means for generating a predetermined Stokes line from the frequency doubled light, the predetermined Stokes line corresponding to a wavelength selected for exciting a phototherapeutic compound.

* * * * *